United States Patent [19]

Vallieres

[11] Patent Number: 5,595,731
[45] Date of Patent: Jan. 21, 1997

[54] ORGANIC FLUID GELIFYING COMPOUNDS

[76] Inventor: Lucien Vallieres, 3001 ouest, rue Sherbrooke bureau 603, Westmount, Canada, H3Z 2X8

[21] Appl. No.: 531,677

[22] Filed: Sep. 21, 1995

Related U.S. Application Data

[63] Continuation-in-part of Ser. No. 216,015, Mar. 21, 1994, abandoned.

[51] Int. Cl.⁶ .................................................. A01N 25/12
[52] U.S. Cl. .................. 424/76.4; 424/76.5; 424/76.6; 424/76.8
[58] Field of Search .................................. 424/76.5, 76.6, 424/76.8, 76.3, 76.4

[56] References Cited

U.S. PATENT DOCUMENTS

| | | | |
|---|---|---|---|
| 4,704,989 | 11/1987 | Rosenfeld | 119/1 |
| 4,853,266 | 8/1989 | Cullen | 206/204 |
| 4,914,066 | 4/1990 | Woodrum | 502/62 |
| 5,078,992 | 1/1992 | Takahashi et al. | 424/76.3 |
| 5,186,946 | 2/1993 | Valliéres | 424/76.6 |
| 5,290,547 | 3/1994 | Bilbrey | 424/76.6 |
| 5,306,487 | 4/1994 | Karapasha | 424/76.6 |

*Primary Examiner*—Amy Hulina
*Attorney, Agent, or Firm*—François Martineau

[57] ABSTRACT

The compound of the invention comprises a combination of four ingredients: a superabsorbent polymer, particularly sodium polyacrylate; a chemical disinfectant, particularly potassium peroxymonosulfate; an organic deodorant, particularly from herbal extracts; and a chelating agent, particularly malic acid. This blood gelifying compound can be used by medical staff in surgery rooms and the like, when wasted blood from the patient is collected in waste bags, to solidify the fluid inside the bag so as to prevent accidental leaks and contamination. Urine or blood spills, which are often accidentally spilled on the hospital floors, can also be recuperated and disposed of in a timely fashion with the present compound, so as not to compromise the hygienic integrity of the hospital.

12 Claims, No Drawings

ORGANIC FLUID GELIFYING COMPOUNDS

CROSS-REFERENCE DATA

This application is a Continuation-In-Part application of U.S. patent application Ser. No. 08/216,015 filed 21 Mar. 1994, now abandoned, in the name of the present inventor and applicant.

FIELD OF THE INVENTION

This invention relates to liquid absorbing compounds for gelifying organic—particularly blood—fluids spilled over ground or stored in waste bags, as well as for concurrently killing microbial agents therein and neutralizing foul odours.

BACKGROUND OF THE INVENTION

In hospitals, contaminated organic materials, such as urine or blood, are often accidentally spilled on the floor. These spills must be recuperated and disposed of in a timely fashion, so as not to compromise the hygienic integrity of the hospital. Also, in surgery rooms and the like, wasted blood from the patient is collected in waste bags, which are ackward in handling and prone to accidental leaks and contamination. These safety concerns have been heightened in the last decade by the emergence of an insidious killer, namely the HIV virus causing a currently irreversible lethal medical condition called Acquired Immuno-Deficiency Syndrome (AIDS). The vector of transmission of the VIH virus includes body-released liquids: blood, sperm and amniotic fluid. The workers in hospitals, particularly maintenance personnel that have to deal with these organic liquid spills on the floor and medical personnel working in surgery rooms, have therefore to regularly handle these organic materials. Clearly, nosocomial contamination can be an implicit concern to these hospital employees, and such concern may reduce the efficiency of their work. This is not desirable, of course.

U.S. Pat. No. 966,060 issued in 1910 to Otis SEVERNS, discloses a compound for cleaning ground scattered dust. This compound includes at least the four following ingredients:

(a) a carrier element (corn cobs);

(b) a dust absorbing, carrier-stabilized element (oil);

(c) a disinfectant; and (d) a perfume.

It is understood that such a ground dust cleaning compound would be ineffective in attempting to capture ground-standing water-based liquid bodies, since water is immiscible in oil due to the hydrophobic features of the oil element in the compound.

A similar drawback is found in U.S. Pat. No. 4,734,393 issued Mar. 29, 1988 to Edward LOWE. In this patent, there is disclosed an absorbing compound for capturing oil and grease, said compound including at least the following ingredients:

(a) an absorbing element (including fibrous plant materials such as citrus pulp and grain); and (b) a disinfectant (of microbicide capability).

In U.S. Pat. No. 4,261,849 issued Apr. 14, 1981 to M. BENJAMINSON, there is disclosed a cleaning compound for cleaning inter alia ground-standing urine and vomit (see column 2, lines 35–40). This compound has the capability of:

(a) absorbing hydrophobic AND hydrophilic materials;

(b) deodorizing by not only masking odours and smells but also by neutralizing the odour producing substances; and (c) at least bacteriostatic effect.

However, such a compound is limited to the following ingredients: alkali metal bicarbonate, alkali metal chloride and fuller's earth.

It is further recognized that current synthetic disposable diapers for infants have been using for a number of years a highly efficient urine-absorbing granular material called sodium polyacrylate. Polyacrylate crystals can absorb up to eighty times their own dry weight in water, while concurrently transforming this water into a gel. This gel then becomes stabilized into the diaper filling, thus preventing accidental outward urine seeping during diaper release from the infant and bin discharge.

OBJECT OF THE INVENTION

The object of this invention is to address the concerns of hospital maintenance crews by both facilitating their work in enabling solidifying of blood and other organic fluids, in containment bags as well as for cleaning liquid organic spills on the ground, wherein the likelihood of nosocomial contamination is substantially decreased.

SUMMARY OF THE INVENTION

The gelifying compound is for use in cleaning liquid water-based organic waste material, and comprises a thoroughly mixed combination of the four following granular ingredients: a) a superabsorbent polymeric element for gelifying the water-based organic waste liquids; b) a deodorant element, said deodorant further cooperating with said polymeric element in stabilizing the gelified waste material; c) a chemical disinfectant of microbicidal properties against all biological material; and d) a chelating agent; wherein said compound promotes easy and timely handling of the liquid waste material during its collection, capture, transportation, and refuse discharge, while substantially precluding cross-contamination and combating foul odours, thanks to the dual deodorizing/stabilizing nature of said deodorizing element.

More particularly, sodium polyacrylate gelifies, i.e. captures liquids by transforming into semi-solid (gel) state any liquid or semi-liquid organic waste material such as vomit, urine, blood, sperm, liquid stools, and exudates, which organic wastes spills are found on floors, beds, upright walls, carpets, furniture and the like. Potassium peroxymonosulfate sanitizes the gelified (captured) organic material. The herbal extracts deodorize the sanitized, gelified material, and further assist in stabilizing the polyacrylate-born gel.

With respect to the chelating agent, to improve solidification of the blood in these bags, it has been discovered that the calcium ions contained in the blood inhibits to a considerable degree the solidifying or gelification of the polymers. Of course, other electrolytes also present in the blood, such as potassium, sodium and magnesium, play a role, but the calcium in the platelets of which 40% are ionized, is the main culprit. Our efforts were directed at using chelating agents in order to remove at least the ionized part of the calcium. Aston-ishing results were obtained, in various media such as urine, Hanks Balanced Saline Solution, and blood, using ethylenediaminetetra-acetic acid disodium salt, ethylene-diaminetetraacetic acid tetra-sodium salt; sulfamic acid; citric acid; gluconic acid; and malic acid.

The four ingredients of the compound, all in powdery form, are to be thoroughly mixed into an homogeneous-compound. The granulometry of the compound would critically remain within the 10 to 800 microns diameter range, whereby an unexpected, particularly performant gelifying capability results; although acceptable performance can be achieved with particle size of up to 4,000μ.

The present gelifying compound therefore facilitates organic waste cleaning in that the four ingredients therein cooperate in a synergistic way to provide an exceptionally performant compound, whereby the following results are achieved:

1) Control of the Liquid Spill

Ground floor may not be exactly level, so that the liquid spill may undesirably flow from one room to another, thus contaminating a larger area than would otherwise be the case. If the liquid spill is on furniture or the like, impregnation of the filler thereof may be substantially reduced or prevented if the gelifying compound is quickly used after spilling action (that is, only superficial water penetration or adsorption would have then occurred). The dry cleaning compound draws under capillarity the liquid to its core.

2) Liquid Absorption

The polyacrylate crystals absorb the aqueous fluid, i.e. binds with same into a gel.

3) Stabilization

The captured waste liquid is stabilized by the herbal extracts forming the deodorizing element of the compound. This stabilized gel is then easier to handle with the cleaning implements of the maintenance crews. By gel handling, there is meant:
   capture;
   lift from ground or other previously stained surface;
   transportation over or relative to said surface; and
   discharge into a refuse bin or sewage system.

Hydrogel formation occurs very rapidly: it has been clocked by the present inventor as taking anywhere between about half a minute to one minute, starting from first contact.

4) Microbicidal Action

This gelifying compound has a 100% lethal action against all biological material with which it comes in contact. Lethality further occurs almost immediately, from first contact with the biological material to nucleic acid damage. The term biological material here is to be construed as including any material capable of self-replication either directly or indirectly, and relates both to living and non living material. Representative examples of living biological material include bacteria, fungi including yeast, algae, protozoa, and the like. Examples of non-living biological material includes viruses, vectors, cell organelles, plasmids and the like material existing in and reproducible solely from a living cell.

5) Deodorizing Action

Foul and nauseous odours are eliminated and neutralized by the plant extract element of the compound.

The present gelifying compound, although particularly advantageous for hospital maintenance crews, is not limited to the human health care environment, since its use could be extended to veterinary clinics, domestic homes, dental clinics, motor vehicles, aircrafts, horse stables, slaughter houses, and the like.

The superabsorbent polymer could alternately consist of cellulosic by-products, starch by-products, polyvinyl alcohol byproducts, cellulosic by-product, and the like. Preferably, this superabsorbent polymer, particularly polyacrylamide or sodium polyacrylate, would further be mixed with some bloated smectic clay, also known as bentonite. Bentonite, from the montmorillonites family $(Al_2O_3.4SiO_2.H_2O)$, and because of its micro-crystallinity, offers some hydrophilic surface sites presenting a high capacity of cationic exchange capable of water absorbency. They form highly viscous suspensions or stable gels.

For the disinfectant, other suitable elemental constituents could include sodium dichlorocyanurate, chloramine, triclosan, quaternary ammonium salts, phenol, calcium hypochlorite, and the like.

The deodorizer could alternately consist of any one of the following ingredients, having a molecular weight preferably under 200 Daltons: hydro-alcoholic extracts, stabilized, steam-distilled, and evaporated to dryness. Said herbal extracts could come from the roots, stems, buds or flowers of the following members of the plant kingdom (the active chemical products embedded therein have been identified after each herbal extract in parentheses):

| | |
|---|---|
| peach tree | $(C_{10}H_{81}O_2)$ and $(C_5H_{10}O)$ |
| maple tree | $(C_7H_{10}O_2)$ and $(C_7H_{10}O_3)$ |
| cucumber | $(C_{10}H_{16}O)$ and $(C_{10}H_{14}O_2)$ |
| azalea | $(C_7H_{16}O)$ |
| angelica | $(C_5H_6O_2)$ |
| cherry tree | $(C_8H_6O_3)$ |
| chestnut tree | $(C_7H_6O_2)$ and $(C_5H_{10}O)$ |
| cedar tree | $(C_{10}H_{81}O)$ and $(C_8H_8O_2)$ |
| cypress | $(C_{10}H_{12}O)$ and $(C_6H_{14}O)$ |
| white birch | $(C_7H_8O)$ and $(C_7H_8O_2)$ |
| strawberry | $(C_{10}H_{01}O_2)$ and $(C_{12}H_{16}O_2)$ |
| butter bur | $(C_9H_{10}O_3)$ and $(C_{10}H_{10}O_4)$ |
| pine tree | $(C_{10}H_{16})$ and $(C_{10}H_{16}O)$ |
| rose | $(C_{12}H_{16}O_2)$ and $(C_{10}H_{18}O)$ |

These herbal extracts are effective for their stated purpose, since they all contain the hydroxyl group or the ester group.

A chelating agent is a chemical compound including a heterocyclic ring containing a metal ion attached by coordinate bonds to at least two nonmetal ions in the same molecule. Some classes of chelating agents include:

polyphosphates: sodium tripolyphosphate, and hexametaphosphoric acid;

aminocarboxylic acids: ethylenediaminetetraacetic acid, hydroxyethylenediaminetriacetic acid, nitrilotriacetic acid, N-dihydroxyethylglycine, and ethylenebis(hydroxyphenylglycine);

1,3-diketones: acetylacetone, trifluoroacetylacetone, and thenoyltrifluoroacetone;

hydroxycarboxylic acids: tartaric acid, citric acid, gluconic acid, and 5-sulfosalicylic acid;

polyamines: ethylenediamine, triethylenetetramine, and triaminotriethylamine;

aminoalcohols: triethanolamine, and N-hydroxyethylethylenediamine;

aromatic heterocyclic bases: dipyridyl, and o-phenanthroline;

phenols: salicylaldehyde, disulfopyrocatechol, and chromotropic acid;

aminophenols: oxine, 8-hydroxyquinoline, and oxinesulfonic acid;

oximes: dimethylglyoxime, and salicyladoxime;

Shiff bases: disalicylaldehyde 1,2-propylenediimine;

tetrapyrroles: tetraphenylporphin, and phthalocyanine;

sulfur compounds: toluenedithiol (Dithiol), dimercaptopropanol, thioglycolic acid, potassium ethyl xanthate, sodium diethyldithiocarbamate, dithizone, diethyl dithiophosphoric acid, and thiourea;

synthetic macrocyclic compounds: dibenzo[18]crown-6(5), $(CH_3)_6[14]4,11$-diene$N_4(6)$, and (2.2.2-cryptate)(7);

polymeric: polyethylenimine, polymethacryloylacetone, and poly(p-vinylbenzyliminodiacetic acid);

phosphonic acids: nitrilotrimethylenephosphonic acid, ethylenediaminetetra(methylenephosphonic acid), and hydroxyethylidenediphosphonic acid.

An important feature of the present gelifying compound is its use in surgery rooms where important quantities of blood are lost. In surgery rooms, e.g., the patient is connected to a suction pump to remove the excess blood in the excision made by the surgeon so that he can see where he is cutting, and must also have a constant unobstructed view at the organs being removed or treated. A tube is connected to a vacuum suction pump and another tube is connected to the top mouth of the suction bag, which is used by a nurse or an assistant in surgery to follow practically the surgeon's knife and pump the blood into the suction bag which is itself held in place by a container. Once the surgery is over, the operating staff is left with one or more bags each containing blood lost during the surgical operation. These bags are considered hazardous materials, the more so in their liquid state; and they are not practical for incineration, because of their fluid state.

To improve solidification of the blood in these bags, it has been discovered that the calcium ions contained in the blood inhibits to a considerable degree the solidifying or gelification of the polymers. Of course, other electrolytes also present in the blood, such as potassium, sodium or magnesium, play a role, but the calcium in the platelets of which 40% are ionized, is the main culprit. Our efforts were directed at using chelating agents in order to remove at least the ionized part of the calcium. Astonishing results were obtained, in various media such as urine, Hanks Balanced Saline Solution, and blood, using ethylenediaminetetraacetic acid disodium salt, ethylenediamine-tetraacetic acid tetrasodium salt; sulfamic acid; citric acid; gluconic acid; and malic acid. The best results were achieved with malic acid, the time required for the gelification of one liter of human blood being reduced by 52% when compared to the use of ethylenediamine-tetraacetic acid disodium salt. This is easily understandable since the use of the sodium salt increases the amount of electrolytes.

The showing of performance criticality of this gelifying compound according to the present invention, is revealed in part by the enhanced absorption capability thereof, which increases relative to standard absorption capability of sodium polyacrylate taken in isolation. More particularly, this is to say that the water absorption capability of the present gelifying compound increases from 80 times—which is the standard value for sodium polyacrylate—to up to 100 times its dry weight. Varying pH values of the environment may slightly affect these performances.

Another showing of criticality appears in the granulometry of the thoroughly mixed dry ingredients in the present compound, which for best results, should be restricted to a range extending between 10 to 800 microns ($10^{-6}$ meter, $\mu$); although still acceptable results could be achieved even with dry particle size reaching up to 4,000$\mu$.

The preferred respective proportions by weight of the various ingredients in the present cleaning compound should be as follows:

(a) superabsorbent polymer: between 5 and 99.99%;

(b) disinfectant: between 0,001 and 60%; and (c) deodorizer: between 0,009 and 35%.

Empirical testing has revealed that the hereinbelow proportions by weight of ingredients for the compound provided excellent results:

disinfectant: 0.7% deodorizer: 18% sodium polyacrylate:
- (a) particle size of 10–400$\mu$: 24.80%
- (b) particle size of 100–600$\mu$: 18.960%
- (c) particle size of 400–800$\mu$: 52.940% malic acid 0.800%

These ingredients, with said empirical testing result values, have demonstrated that the present gelifying compound has the following properties:

100% bactericidal lethality on *Bacillus subtilis* and on *Escherichia coli* within one minute timeline;

low skin-irritation;

good chemical stability;

no side effect produced when the potassium peroxymonosulfate becomes accidentally admixed with alkaline or acidic substances (i.e. release to the environment of free chlorine or other noxious gases does not occur).

Once the blood is solidified in the bag, it is much easier to handle and offers much less danger to the person carrying the bag, since the blood cannot spill out or leak because of its solid state, the importance of the bactericidal activity and the absence of undesirable odor. The product is dispersed in specially designed bottles with caps adapted to suction bags, as soon as the blood reaches the bottom of the bag, it is solidified or gelified, disinfected and rendered odorless.

I claim:

1. A gelifying compound for use in solidifying liquid water-based organic material, and comprising a thoroughly mixed combination of the four following ingredients:

a) a granular superabsorbent polymer, for gelifying the water-based organic waste material into a gel;

b) a non-metallic deodorizer having inherent means for cooperating with said polymer in stabilizing said gel, said inherent stabilizing means consisting of herbal extracts from the roots, stems, buds or flower of the following group of members of the plant kingdom: peach tree, maple tree, cucumber, azalea, angelica, cherry tree, chestnut, rose, pine, cedar, cypress, white birch, strawberry, and butterbur, said herbal extracts substantially enhancing the water absorbing capability of said polymer wherein stabilization of the gelified waste material is improved together with ease of handling thereof;

c) a granular chemical disinfectant, having microbicidal properties against all biological material; and (d) a chelating agent, for neutralizing calcium ions contained in the organic material so as to enhance gelification of the polymer;

wherein said compound promotes easy and timely handling of the liquid organic material during its collection, capture, transportation, and refuse discharge, while substantially precluding cross-contamination and combating foul odours, thanks to the dual deodorizing/stabilizing nature of said deodorizer.

2. An organic fluid gelifying compound as defined in claim 1, wherein the granulometry of the granular elements in said compound does not exceed 4,000 microns.

3. An organic fluid gelifying compound as defined in claim 2, wherein said granulometry of the granular elements in said compound is restricted to a range extending between 10 to 800 microns.

4. An organic fluid gelifying compound as defined in claim 1, wherein the respective proportions by weight of the various ingredients in the present cleaning compound are as follows:

(a) superabsorbent polymer: between 4.99 and 94.99%;

(b) disinfectant: between 0.001 and 60%;

(c) deodorizer: between 0.009 and 35%; and (d) chelating agent: between 0.01 and 5%.

5. An organic fluid gelifying compound as defined in claim 1, wherein the disinfectant is selected from the group comprising potassium peroxymonosulfate, sodium dichlorocyanurate, chloramine, triclosan, quaternary ammonium salts, phenol, calcium hypochlorite, and sodium hypochlorite.

6. An organic fluid gelifying compound as defined in claim 4, wherein said superabsorbent polymer is sodium polyacrylate.

7. An organic fluid gelifying compound as defined in claim 6, further including a small proportion, relative to the other ingredients in said compound, of bloated smectic clay, being thoroughly mixed with the other ingredients.

8. An organic fluid gelifying compound as defined in claim 6, wherein the respective proportions by weight of the ingredients are as follows:

disinfectant: 0.7% deodorizer: 1.80% sodium polyacrylate:
  (a) particle size of 10–400 microns: 24.800%
  (b) particle size of 100–600 microns: 18.960%
  (c) particle size of 400–800 microns: 52.940% chelating agent: 0.800%.

9. An organic fluid gelifying compound as in claim 1, wherein said chelating agent is chosen from the group consisting of:

(a) EthyleneDiamineTetraAcetic acid disodium salt;

(b) EthyleneDiamineTetraAcetic acid tetrasodium salt;

(c) sulfamic acid;

(d) citric acid;

(e) gluconic acid; and (f) malic acid.

10. An organic fluid gelifying compound as in claim 9, wherein said chelating agent is malic acid.

11. An organic fluid gelifying compound as defined in claim 10, wherein the respective proportions by weight of the ingredients are as follows:

disinfectant: 0.7% deodorizer: 1.800% sodium polyacrylate:
  (a) particle size of 10–400 microns: 24.800%
  (b) particle size of 100–600 microns: 18.960%
  (c) particle size of 400–800 microns: 52.940% malic acid: 0.800%.

12. An organic fluid gelifying compound as defined in claim 11, wherein the organic fluid is human blood.

* * * * *